(12) United States Patent
Bidi et al.

(10) Patent No.: US 12,687,547 B2
(45) Date of Patent: Jul. 21, 2026

(54) BIOCHEMICAL MEDICAL DIAGNOSTIC KIT

(71) Applicant: ARGERON MEDIKAL ARASTIRMA SANAYI VE TICARET ANONIM SIRKETI, Dosemealti (TR)

(72) Inventors: Bülent Bidi, Döşemealti (TR); Abdullah Olgun, Döşemealti (TR)

( * ) Notice: Subject to any disclaimer, the term of this patent is extended or adjusted under 35 U.S.C. 154(b) by 532 days.

(21) Appl. No.: 18/264,591

(22) PCT Filed: Mar. 1, 2022

(86) PCT No.: PCT/TR2022/050179
§ 371 (c)(1),
(2) Date: Aug. 8, 2023

(87) PCT Pub. No.: WO2022/186803
PCT Pub. Date: Sep. 9, 2022

(65) Prior Publication Data
US 2024/0110923 A1 Apr. 4, 2024

(30) Foreign Application Priority Data
Mar. 5, 2021 (TR) ............................... 2021/004329

(51) Int. Cl.
*G01N 33/68* (2006.01)

(52) U.S. Cl.
CPC ..... *G01N 33/6848* (2013.01); *G01N 2440/16* (2013.01)

(58) Field of Classification Search
None
See application file for complete search history.

(56) References Cited

U.S. PATENT DOCUMENTS

| | | | |
|---|---|---|---|
| 5,273,886 A | 12/1993 | Aswad | |
| 2005/0176085 A1* | 8/2005 | Betancourt Nunez | G01N 33/6848 435/23 |
| 2019/0360980 A1* | 11/2019 | Graham | G01N 33/5005 |
| 2021/0391030 A1* | 12/2021 | Pastrana-Rios | C07K 16/00 |
| 2022/0133838 A1* | 5/2022 | Kenney | A61K 38/095 514/10.9 |
| 2023/0017454 A1* | 1/2023 | Yan | G01N 33/6854 |
| 2023/0204595 A1* | 6/2023 | Daud | G01N 33/6848 436/86 |
| 2023/0375565 A1* | 11/2023 | Zhang | G01N 33/6845 |
| 2024/0029819 A1* | 1/2024 | Merbl | C07K 7/06 |
| 2024/0036056 A1* | 2/2024 | Zhang | C07K 1/00 |

(Continued)

OTHER PUBLICATIONS

International Search Report and Written Opinion of the International Searching Authority ffor corresponding PCT/TR2022/050179 dated Jun. 8, 2022.

(Continued)

*Primary Examiner* — Brian R Gordon
(74) *Attorney, Agent, or Firm* — EGBERT, MCDANIEL & SWARTZ, PLLC

(57) ABSTRACT

Disclosed is a deamidation rate measurement kit, which includes a stock solution of the compound Boc-Asn-Gly-OEt in deionized/distilled water, and a stock solution of the compound Boc-Asp-Gly-OEt in deionized/distilled water.

8 Claims, 1 Drawing Sheet

(56) References Cited

U.S. PATENT DOCUMENTS

2024/0053359 A1 * 2/2024 Wang ................. G01N 33/6854
2024/0060991 A1 * 2/2024 Yates ................. G01N 33/6803

OTHER PUBLICATIONS

Kameoka et al., "A method for the detection of asparagine deamidation and aspartate isomerization of proteins by MALDI/TOF-mass spectrometry using endoproteinase Asp-N.", Journal of biochemistry, Jul. 1, 2003, pp. 129-135.

Terashima et al., "Identification of deamidation and isomerization sites on pharmaceutical recombinant antibody using H218O", Analytical biochemistry, 2007, 368.1: 49-60., Sep. 1, 2007.

* cited by examiner

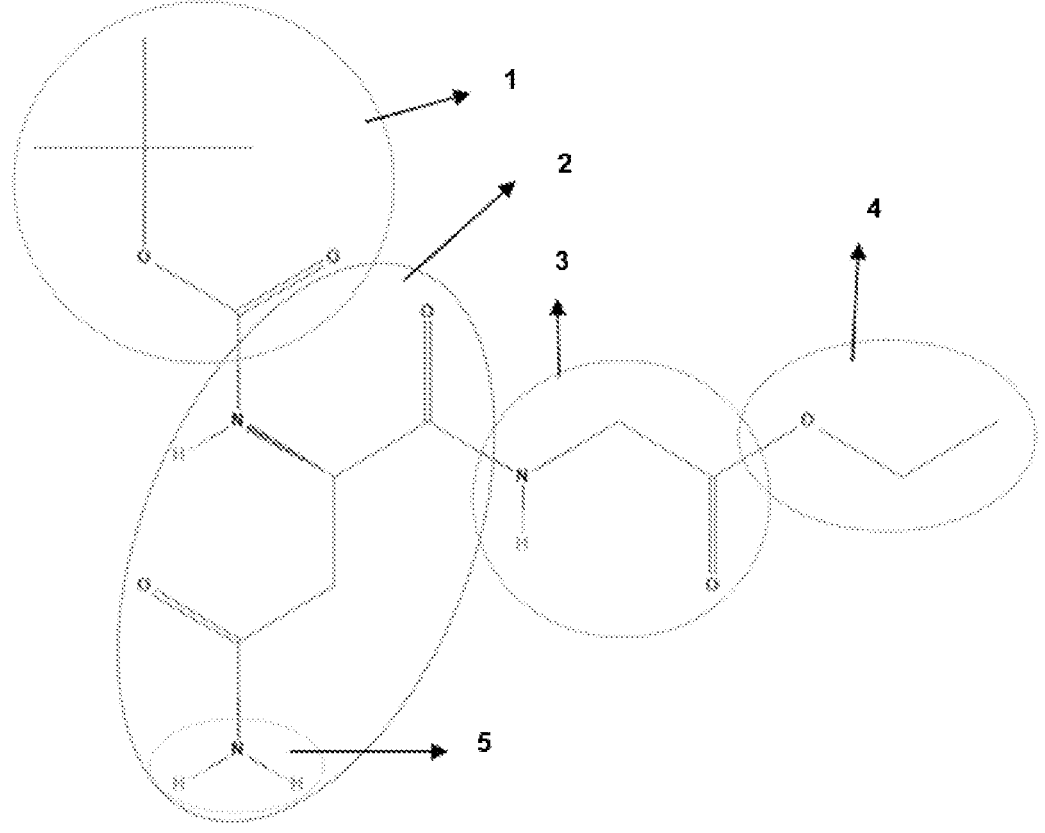

BIOCHEMICAL MEDICAL DIAGNOSTIC KIT

TECHNICAL FIELD

The invention relates to a kit suitable for biological samples in the field of in vitro diagnostics (biochemical medical diagnosis, etc.) or for use in other fields (pharmacy, chemistry, etc.).

In particular, the invention relates to a kit suitable for use to measure the effect of solutions on the deamidation rate of the proteins they contain.

STATE OF THE ART

Proteins are one of the basic structural and functional molecules that make up living organisms. Proteins are large organic compounds that are formed as a result of the binding of amino acids to each other in chains. Peptides are short polymers formed by linking α-amino acids in a defined order. The bond between one amino acid residue and another is known as an "amide bond" or peptide bond. Proteins are polypeptide molecules (or contain multiple polypeptide sub-units). The main difference is that peptides are short while polypeptides/proteins are long.

Asparagine (Asp, N) and glutamine (Gln, Q), two of the 20 different amino acids in the structure of proteins, have amide groups in their side chains. Removal of amide groups in proteins containing these amino acids is called protein deamidation. Protein deamidation can occur enzymatically or spontaneously. As a result of deamidation, changes occur in the structure and charge of proteins. As a result of deamidation, especially in long-lived proteins found in long-lived cells such as neurons, deamidated proteins may accumulate over time, causing structural and functional disorders in these proteins and therefore in the cells in which these proteins are present. A great deal of scientific evidence supporting the role of protein deamidation in Alzheimer's, frontotemporal dementia and many other chronic diseases has been reported in the literature.

For this reason, it is necessary to determine the factors or interventions that affect the deamidation rate, to develop strategies that can prevent/slow down deamidation, and to determine the deamidation rates in individuals. In this way, it is expected that they can make very critical contributions to the prevention and postponing of aging and age-related diseases.

Deamidation is an important factor not only in aging, but also in the stability of protein-containing pharmaceutical drugs (such as vaccines). It is necessary to measure the effect of the solutions in which these drugs are dissolved on the protein deamidation rate, and to make interventions to slow the deamidation rate when added to the solutions. In the state of the art, there are studies on this subject.

U.S. Pat. No. 5,273,886 The invention relates to methods and tools for the quantitative determination of the isoaspartyl content of polypeptides by selective methylation of their fragments catalyzed by a protein L-isoaspartyl methyltransferase enzyme. Since the deamidation of asparagine side chains at certain protein sites and the resulting isoaspartate formation appear to be an important contributor to protein degradation under mild conditions, the invention also relates to a method for quantifying protein degradation associated with isoaspartate formation.

Although there are studies on this subject in the state of the art, they only allow to indirectly analyze the components found in the interior of pure proteins. Since it can only be used to measure the deamidation of purified proteins, it cannot be used for biological samples with more complex matrices such as blood plasma. There is still no test method that can be used to measure the effect of biological samples (serum, plasma, saliva, cerebrospinal fluid, synovial fluid, urine, cell/tissue/organ extracts, etc.) of humans and other living things on the rate of protein deamidation. For this reason, there is a need to develop a test that has the potential to be used in medical biochemistry laboratories, to measure the effect of biological samples on the protein deamidation rate and to detect interventions that affect the deamidation rate.

As a result, due to the negativities described above and the inadequacy of the existing solutions on the subject; It has been necessary to develop kits that measure the deamidation rate.

AIM OF THE INVENTION

The present invention relates to a deamidation rate measurement kit that meets the above-mentioned requirements, eliminates all disadvantages and brings some additional advantages.

The primary aim of the invention is to develop a kit that measures the effect on the deamidation rate when added to solutions containing protein pharmaceuticals.

One aim of the invention is to develop a measurement kit that enables to determine the factors affecting the deamidation rate, to examine the correlation of individual differences in deamidation rate with aging and age-related diseases, and to detect diseases characterized by an increase in deamidation rate.

To fulfill the above-described purposes, the invention is a deamidation rate measurement kit containing a stock solution in deionized/distilled water containing the compound Boc-Asn-Gly-OEt and a stock solution in deionized/distilled water containing the compound Boc-Asp-Gly-OEt.

The structural and characteristic features of the invention and all its advantages will be understood more clearly thanks to the detailed explanation written below, and therefore the evaluation should be made by taking this detailed explanation into consideration.

FIGURES TO HELP EXPLAIN THE INVENTION

FIG. 1: Structure of the Boc-Asn-Gly-OEt compound

| Explanation of References | |
| --- | --- |
| 1 | Boc- |
| 2 | Asn |
| 3 | Gly |
| 4 | -Oet |
| 5 | Region being deamidated |

DETAILED EXPLANATION OF THE INVENTION

In this detailed explanation, the deamidation rate measurement kit, which is the subject of the invention, is explained only for a better understanding of the subject and without causing any limiting effect.

The deamidation rate measurement kit, which is the subject of the invention, in its most basic form; contains stock solution in deionized/distilled water containing the compound Boc-Asn-Gly-OEt (preferably in the range of 0.000001-1000 mM, more preferably at the concentration of 0.25 mM) and stock solution in deionized/distilled water containing the compound Boc-Asp-Gly-OEt (preferably 0.000001-1000 mM) mM, more preferably at a concentration of 0.25 mM).

The Boc-Asn-Gly-OEt compound, a sample view of which is given in FIG. 1, is used both as a calibrator and analytical standard in measurements, and as a deamidated element by being added to biological samples. Boc- (1) and -Oet (4) are for blocking Asparagine (Asn) (2) and glycine (Gly) (3) dipeptides respectively, as details shown in the FIGURE. In the deamidated region (5) shown in the FIGURE, the "NH2" structure is removed by deamidation, while the "OH" structure is attached instead. Thus, the Boc-Asn-Gly-OEt compound turns into the Boc-Asp-Gly-OEt compound and its molecular weight increases by about 1 (0.98) g/mol. Boc- (1) and -OEt (4) structures-in the structure of the Boc-Asn-Gly-OEt compound in solution—allow to block the binding of Asn (2) and Gly (3) dipeptides with unwanted chemical groups during the process. The Asn (2) and Gly (3) dipeptides are one of the structures with the fastest spontaneous deamidation known. For this reason, it is used in measurements as as the calibrator/analytical standard or the compound subject to deamidation after adding to biological samples. Since Boc-Asn-Gly-OEt is converted into Boc-Asp-Gly-OEt compound as a result of spontaneous deamidation, Boc-Asp-Gly-OEt compound is used as Calibrator and analytical standard in drawing the calibration curve. The Boc-Asp-Gly-OEt compound is not commercially available but has been specially synthesized. Deionized/distilled water allows to dissolve Boc-Asn-Gly-OEt and Boc-Asp-Gly-OEt compounds and is used as analytical blank.

In a sample application of the invention, the deamidation rate measurement kit developed includes the following steps of process: Preparation of stock solution and serial dilutions of Boc-Asn-Gly-OEt compound in deionized/distilled water; Preparation of stock solution and serial dilutions of Boc-Asp-Gly-OEt compound in deionized/distilled water; Creation of the calibration curve on the instrument to be measured using serial dilutions of the Boc-Asn-Gly-OEt stock solution; Creation of the calibration curve on the instrument to be measured using serial dilutions of the Boc-Asp-Gly-OEt stock solution; aliquoting the biological sample whose effect on the deamidation rate will be tested in equal volumes in three different tubes; addition—preferably in the range of 1/1000-1/2 of the final reaction volume (more preferably in the range of 1/10)—of Boc-Asn-Gly-OEt and Boc-Asp-Gly-OEt (as an internal standard) stock solutions to different tubes, and of deionized/distilled water to another tube as blank; at the beginning of the measurement, making measurements from all three tubes, preferably by LC-MS method; after incubation making measurements of all three tubes, preferably by LC-MS method; subtraction of the measurement results in the tubes with added Boc-Asn-Gly-OEt and Boc-Asp-Gly-OEt from the measurement in the tube with deionized/distilled water; determination of deamidation rate by measuring Boc-Asp-Gly-OEt resulting from spontaneous deamidation in the tube with added Boc-Asn-Gly-OEt.

The present invention is based on the principle of spontaneous deamidation of Boc-Asn-Gly-OEt compound in solution into Boc-Asp-Gly-OEt compound and measuring the resulting Boc-Asp-Gly-OEt compound by an appropriate analytical method. Boc-Asn-Gly-OEt solution is added to any sample whose effect on the spontaneous deamidation rate is desired to be measured. Spontaneous deamidation of Boc-Asn-Gly-OEt in this mixture, which is kept at a temperature between 1-100° C. for 1 minute-1 month, is ensured. During the incubation period, as a result of the deamidation of the Boc-Asn-Gly-OEt dipeptide in the mixture, the—$NH_2$ group [FIG. 1:(5)] will spontaneously be released from the molecule, while the asparagine in the compound will be converted to isoaspartate or aspartate with the addition of the —OH group, and a molecular weight increase of approximately 1 (0.98) g/mol mass will occur. This change in mass, that is, the resulting Boc-Asp-Gly-OEt and Boc-Isoasp-Gly-OEt can be measured by mass spectrometry, as well as with all kinds of optimized methods based on the different chemical properties of the —$NH_2$ group in the asparagine of the compound and the —OH group of the newly formed aspartate in the compound.

By measuring the effect of the biological samples from individuals/patients on the deamidation rate by using the deamidation rate measurement test, which is the subject of the present invention, and by examining the correlation of individual differences—to be detected and that affect the deamidation rate—with aging and age-related diseases, and if diseases characterized by an increase in deamidation rate are detected, the test is provided to be used as a marker to determine the susceptibility to these diseases and for their early diagnosis.

The invention claimed is:

1. A deamidation rate measurement kit comprising:
   a first stock solution including deionized/distilled water containing Boc-Asn-Gly-OEt compound and
   a second stock solution including deionized/distilled water containing Boc-Asp-Gly-OEt compound.

2. The kit according to claim 1, wherein the first stock solution has a concentration of the Boc-Asn-Gly-OEt compound in a range of 0.000001-1000 mM.

3. The kit according to claim 2, wherein the concentration is 0.25 mM.

4. The kit according to claim 1, wherein the second stock solution has a concentration of the Boc-Asp-Gly-OEt compound in a range of 0.000001-1000 mM.

5. The kit in accordance with claim 4, wherein the concentration is 0.25 mM.

6. A rate measurement method of making and using the deamidation rate measurement kit in accordance claim 1 to determine a deamidation rate, the method, comprising:
   making the first stock solution by serial dilutions of the Boc-Asn-Gly-OEt compound in deionized/distilled water;
   making the second stock solution by serial dilutions of the Boc-Asp-Gly-OEt compound in deionized/distilled water;
   creating a calibration curve on an instrument to be measured using the serial dilutions of the first Boc-Asn-Gly-OEt stock solution;
   and the serial dilutions of the second Boc-Asp-Gly-OEt stock solution;
   aliquoting a biological sample that has effect on the deamidation rate in equal volumes in three different sample tubes;
   adding the first Boc-Asn-Gly-OEt stock solution to one of the three sample tubes, the second Boc-Asp-Gly-OEt, a standard, stock solution to a second tube of the three sample tubes, and deionized/distilled water to a third tube of the three sample tubes, in the range of 1/1000-1/2 of a final reaction volume;
   making measurements and obtaining measurement results of all three sample tubes;
   incubating the three sample tubes;

after incubating the three sample tubes, making and obtaining measurements of the three sample tubes; and subtracting the measurement results of the first and second sample tubes with the added Boc-Asn-Gly-OEt and Boc-Asp-Gly-OEt from the measurement in the sample tube with the added deionized/distilled water;

determining the deamidation rate by measuring Boc-Asp-Gly-OEt, which is formed as a result of spontaneous deamidation in the first sample tube with the added Boc-Asn-Gly-OEt.

7. The method according to claim 6, wherein all of the measurements are made by using a LC-MS method.

8. The method according to claim 6, wherein the final reaction volume is 1/10.

* * * * *